United States Patent [19]

Woods et al.

[11] Patent Number: 4,657,160

[45] Date of Patent: Apr. 14, 1987

[54] PRESSURE INFUSION CONTROL

[76] Inventors: Andy Woods, 400 L.P.Mann Dr., Marion, Ark. 72364; Peter T. Giannini, 3921 Hermitage, Memphis, Tenn. 38116

[21] Appl. No.: 820,935

[22] Filed: Jan. 21, 1986

Related U.S. Application Data

[63] Continuation-in-part of Ser. No. 650,076, Sep. 13, 1984, abandoned.

[51] Int. Cl.⁴ .......................... A61M 5/00; B65D 35/28
[52] U.S. Cl. ................................ 222/94; 128/DIG. 12; 222/95; 222/105; 222/334; 222/386.5; 222/389; 222/396; 222/397; 222/399; 604/141; 604/147
[58] Field of Search ...................... 222/53, 61, 95, 105, 222/214, 334, 386.5, 389, 394, 396, 397, 399; 128/DIG. 12; 604/140–142, 146, 147; 100/211, 269 R; 417/46

[56] References Cited

U.S. PATENT DOCUMENTS

| | | | |
|---|---|---|---|
| 3,209,680 | 10/1965 | McGinnis | 222/386.5 X |
| 3,640,276 | 2/1972 | Dancy, Jr. | 222/61 X |
| 3,640,277 | 2/1972 | Adelberg | 222/61 X |
| 3,895,741 | 7/1975 | Nugent | 222/389 X |
| 4,191,184 | 3/1980 | Carlisle | 222/61 X |
| 4,430,078 | 2/1984 | Sprague | 222/95 X |
| 4,487,335 | 12/1984 | Bonerb | 222/61 X |

FOREIGN PATENT DOCUMENTS

1144162  3/1969  United Kingdom ................. 52/197

Primary Examiner—Joseph J. Rolla
Assistant Examiner—Kevin P. Shaver
Attorney, Agent, or Firm—Walker & McKenzie

[57] ABSTRACT

A pressure infusion system including a flexible bag containing a quantity of liquid to be infused, a pressure cuff for causing the liquid to be forced from the bag, and a control assembly for controlling the pressure cuff. The control assembly includes a manually operative valve for allowing pressurized gas to inflate the pressure cuff to force liquid from the bag, and for allowing a vacuum to be applied to the pressure cuff to quickly deflate the pressure cuff.

4 Claims, 11 Drawing Figures

PRESSURE INFUSION CONTROL

CROSS-REFERENCE TO RELATED APPLICATION

This is a continuation-in-part of our now abandoned application, Ser. No. 06/650,076, filed Sept. 13, 1984, entitled "Pressure Infusion Control".

BACKGROUND OF THE INVENTION

1. Field of the Invention

The present invention relates, in general, to pressure infusion systems for allowing fluid to be infused into a patient.

2. Description of the Prior Art

Heretofore, various pressure infusion systems have been developed. See, for example, Wallace, U.S. Pat. No. 2,766,907; Beall, U.S. Pat. No. 3,153,414; Dancy, U.S. Pat. No. 3,640,276; Adelberg, U.S. Pat. No. 3,640,277; Bannister, U.S. Pat. No. 3,756,459; Hinck, U.S. Pat. No. 4,090,514; and Andreas, U.S. Pat. No. 4,270,533. None of the above patents disclose or suggest the present invention.

SUMMARY OF THE INVENTION

The present invention is directed toward providing an improved pressure infusion system. The concept of the present invention is to provide a control means which utilizes the typical pressurized gas supply means commonly available in hospitals and the like to allow the typical pressure infusion cuff to be quickly inflated and subsequently quickly deflated.

The improved system of the present invention is of the type including a pressure means for applying pressure to a flexible bag containing a quantity of liquid to be infused, wherein the improvement comprises, in general, means for supplying pressurized fluid to the pressure means to cause the pressure means to apply pressure to the bag to force the liquid from the bag and for applying a vacuum to the bag to quickly remove the pressurized fluid from the bag, and control means having a first position for allowing pressurized fluid to be supplied to the pressure means and having a second position for allowing a vacuum to be applied to the pressure means.

One object of the present invention is to speed and facilitate the inflation and subsequent deflation of inflatable pressure infusion cuffs. Another object of the present invention is to speed up the replacement of lost blood and the like. Another object of the present invention is to provide for the active evacuation of pressure infusion cuffs as opposed to the typical passive evacuation thereof.

DESCRIPTION OF THE PREFERRED EMBODIMENT

A first embodiment of the present invention is shown in FIGS. 1-5. The pressure infusion system 11 of the first embodiment of the present invention is of the type that includes a flexible bag 13 for containing a quantity of liquid to be infused and a pressure means 15 for selectively applying pressure to the bag 13 to force the liquid from the bag 13. The bag 13 and pressure means 15 may be of any typical construction now known to those skilled in the art. Thus, the bag 13 may consist of the conventional liquid-filled, flexible plastic bag which can contain various infusible fluids necessary for a patient during surgical or emergency procedures such as, for example, crystalloids, blood, or other colloids. A tube 17 extends from the bag 13 to a needle 19 for being inserted into a patient's body. A filter 21 may be provided between the bag 13 and needle 19. The pressure means 15 may consist of any typical, well-known pressure infusion cuff having a bag-like body 23 for receiving the bag 13 and having an inflatable bladder 25 mounted with respect to the body 23 in such a manner so that the fluid will be forced from the bag 13 when the bag 13 is positioned in the body 23 and bladder 25 is inflated. The bladder 25 is provided with a port 27 for allowing air to be forced into the bladder 25 to inflate the bladder 25 and to exit the bladder 25, thus allowing the bladder 25 to deflate. In the prior art, a hand or foot operated bulb (not shown) is typically connected to the port 27 by a flexible tube to allow the bladder 25 to be manually inflated. A relief valve, or the like, is typically associated with the bulb to allow the bladder 25 to passively evacuate or deflate. The specific construction of the bag 13 and pressure means 15 may vary as will be apparent to those skilled in the art. One such typical construction is disclosed by Dancy, U.S. Pat. No. 3,640,276 in FIGS. 7, 10 and 11 thereof and identified generally as a transfusion unit 102 including a pressure cuff 118 having an upwardly open pocket-like portion 120 affixed thereto to serve as a receptacle for a flexible fluid container 122. Reference should be made to the Dancy U.S. Pat. No. 3,640,276 patent for a more detailed disclosure thereof if desired.

The system 11 includes a pressurized fluid means 29 (see, in general, FIG. 1) for supplying pressurized fluid to the pressure means 15 to cause the pressure means 15 to apply pressure to the bag 13 to force the liquid from the bag 13. The term pressurized fluid as used herein includes pressurized air, pressurized gas, and the like. The pressurized fluid means 29 preferably consists of the typical pressurized gas source commonly available in hospitals and the like to supply oxygen and the like to a patient. Thus, the pressurized fluid means 29 preferably includes a pressurized gas outlet port 31 mounted on a panel 33 or the like provided on the wall 35 of a hospital room or the like as is well known to those skilled in the art.

The system 11 also includes a vacuum means 37 (see, in general, FIG. 1) for quickly removing the pressurized fluid from the pressure means 15. The vacuum means 37 preferably consists of the typical vacuum source typically available in hospitals, and the like. Thus, the vacuum means 37 commonly includes a vacuum fluid or gas inlet port 39 provided on a panel 40 provided on the wall 35 of the hospital room adjacent the pressurized fluid outlet port 31 as is well-known to those skilled in the art.

The ports 31, 39 may consist of typical plug-in receptacle type connection means well known to those skilled in the art.

The system 11 includes a control means 41 (see FIGS. 1, 3, 4 and 5) for controlling the pressurized fluid means 29 and the vacuum means 37 with respect to the pressure means 15. The control means 41 includes at least one valve means 43 for being coupled to both the pressurized gas outlet port 31 and vacuum fluid inlet port 39 and to the port 27 of the bladder 25 of the pressure means 15 to selectively allow communication between the pressurized fluid means 29 and pressure means 15 to quickly inflate the bladder 25 and between the vacuum means 37 and the pressure means 15 to subsequently quickly and positively deflate the bladder 25.

The control means 41 preferably includes a box-like housing member 45 which may be constructed of cast aluminum or the like with the valve means 43 mounted therein. The housing member 45 is preferably provided with a pressurized gas port 47 for communicating with the pressurized fluid outlet port 31, a vacuum port 49 for communicating with the vacuum fluid inlet port 39, and at least one outlet port 51 for communicating with the port 27 of the bladder 25. The various ports 47, 49, 51 may be of any typical construction now apparent to those skilled in the art. Thus, each port 47, 49, 51 may consist of a typical one-eighth inch (3.175 millimeters) barbed nipple well-known to those skilled in the art for allowing the end of a rubber hose or the like to be pushed thereonto.

A pressurized gas inlet conduit means 53 is provided to couple the pressurized gas port 47 to the pressurized gas outlet port 31. The pressurized gas inlet conduit means 53 may include a one-fourth inch (6.35 millimeters) inside diameter rubber hose with appropriate adapters to connect to the ports 31, 47. Thus, the conduit means 53 has a first end for being attached to the pressurized gas inlet port 47 by being pushed thereover and has a second end to which a plug-in type connection means 55 is attached to allow the pressurized gas inlet conduit means 53 to be operatively coupled to the plug-in type connection means of the pressurized gas outlet port 31.

A vacuum inlet conduit means 57 is provided to allow the vacuum port 49 to be operatively coupled to the vacuum fluid inlet port 39. The vacuum inlet conduit means 57 may also include a one-fourth inch (6.35 millimeters) inside diameter rubber hose having a first end for being attached to the vacuum port 49 by being pushed thereover and having a second end for being attached to a plug-in type connection means of the vacuum fluid inlet port 39.

A conduit 61 is provided for coupling the outlet port 51 to the port 27 of the bladder 25. Thus, the conduit 61 may consist of a one-fourth inch (6.35 millimeters) inside diameter rubber hose having a first end for being pushed over the outlet port 51 and having a second end for being coupled to the port 27 of the bladder 25. The conduit 61 may consist of the typical conduit commonly provided as a part of the bladder 25 of pressure means 15.

The control means 41 includes passageway means for operatively coupling the valve means 43, pressurized gas inlet port 47, vacuum port 49 and outlet port 51 to allow the passage of fluid therebetween. The valve means 43 is preferably a typical three-position, three-way ball valve having a closed position in which the passageway between the outlet port 51 and both the pressurized gas inlet port 47 and the vacuum port 49 is closed to occlude the flow of fluid through the control means 41, having a first open position in which the passageway means between the outlet port 51 and the pressurized gas inlet port 47 is opened while the passageway means between the vacuum port 49 and the outlet port 51 is closed to allow fluid to pass from the pressurized gas inlet port 47 through the control means 41 to the outlet port 51 while occluding the passageway means between the outlet port 51 and vacuum port 49, and a second open position in which the passageway means between the outlet port 51 and the vacuum port 49 is opened while the passageway means between the pressurized gas inlet port 47 and the outlet port 51 is closed to allow gas to be quickly drawn through the vacuum port 49 while occluding passage of gas from the pressurized gas inlet port 47 through the control means 41. A control knob 63 is preferably coupled to the valve means 43 and positioned on the exterior of the housing member 45 to allow manual movement of the valve means 43 between the three positions.

The control means 41 preferably includes a regulator means 65 (see FIG. 5) for regulating the pressure of the pressurized gas as it passes therethrough the control means 41. The regulator means 65 preferably consists of any typical, well-known pressure regulator for regulating the input air pressure and to provide a predetermined output air pressure despite any fluctuations in input gas pressure from the pressurized fluid means 29. Thus, the regulator means 65 preferably maintains the positive pressure of the system 11 at a constant 300 millimeters of mercury (5.8 pounds per square inch gauge). The regulator means 65 is preferably positioned within the passageway means between the pressurized gas inlet port 47 and the valve means 43.

The control means 41 preferably includes a high pressure relief valve means 67 (see, in general, FIG. 5) for preventing the pressure of the pressurized gas passing therethrough from exceeding a predetermined amount as it is supplied to the pressure means 15. The high pressure relief valve means 67 may be of any typical construction apparent to those skilled in the art and is preferably set to open to atmosphere should the pressure exceed ten percent of the regulated valve. The high pressure relief valve means 67 is preferably positioned within the passageway means between the regulator means 65 and the valve means 43.

Figure 5:
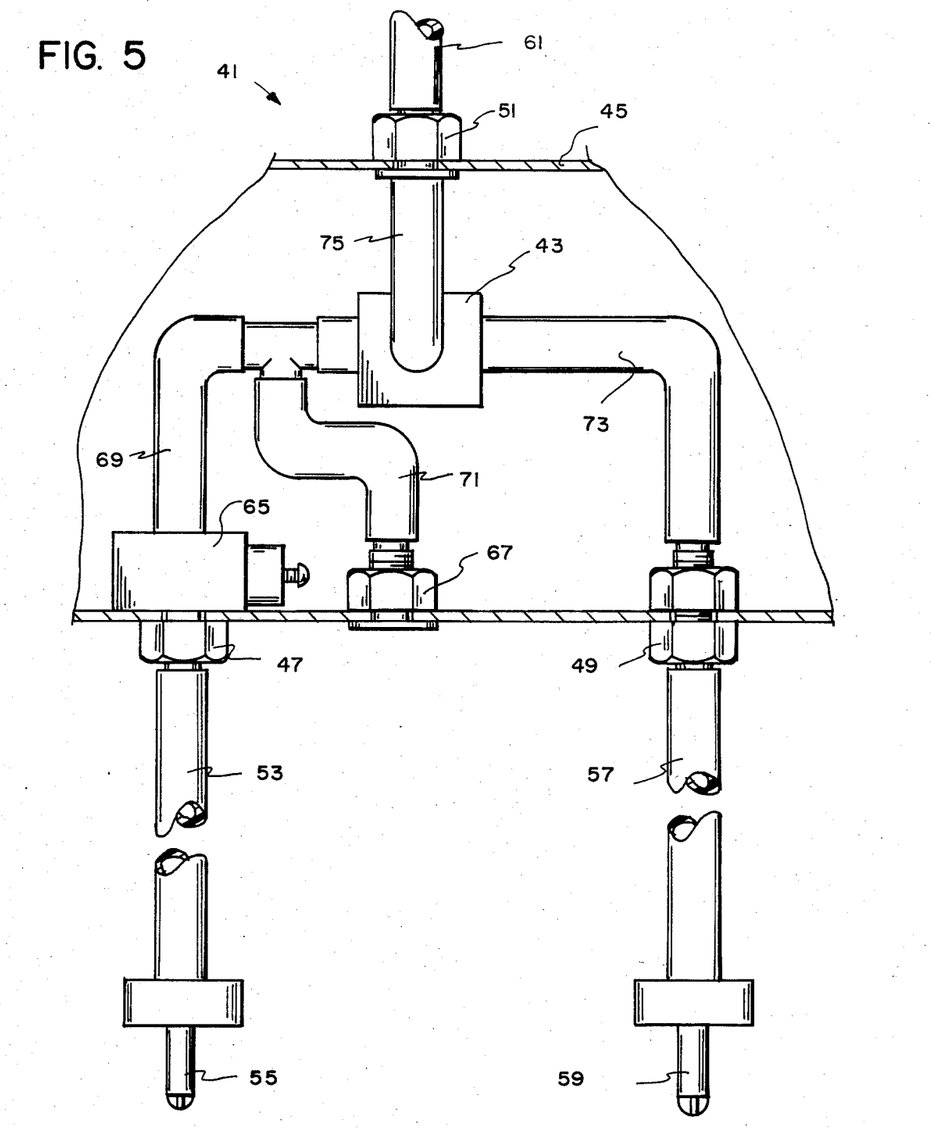
FIG. 5 is a sectional view of a portion of the control means and associated structure of the system of FIG. 1.

The regulator means 65 may be attached directly to the pressurized gas inlet port 47 and the passageway means may be defined by a first conduit member 69 extending between the regulator means 65 and the valve means 43, a second conduit member 71 extending between the high pressure relief valve means 67 and the first conduit member 69, a third conduit member 73 extending between the vacuum port 49 and the valve means 43, and a fourth conduit member 75 extending between the valve means 43 and the outlet port 51 (see FIG. 5).

Figure 1:
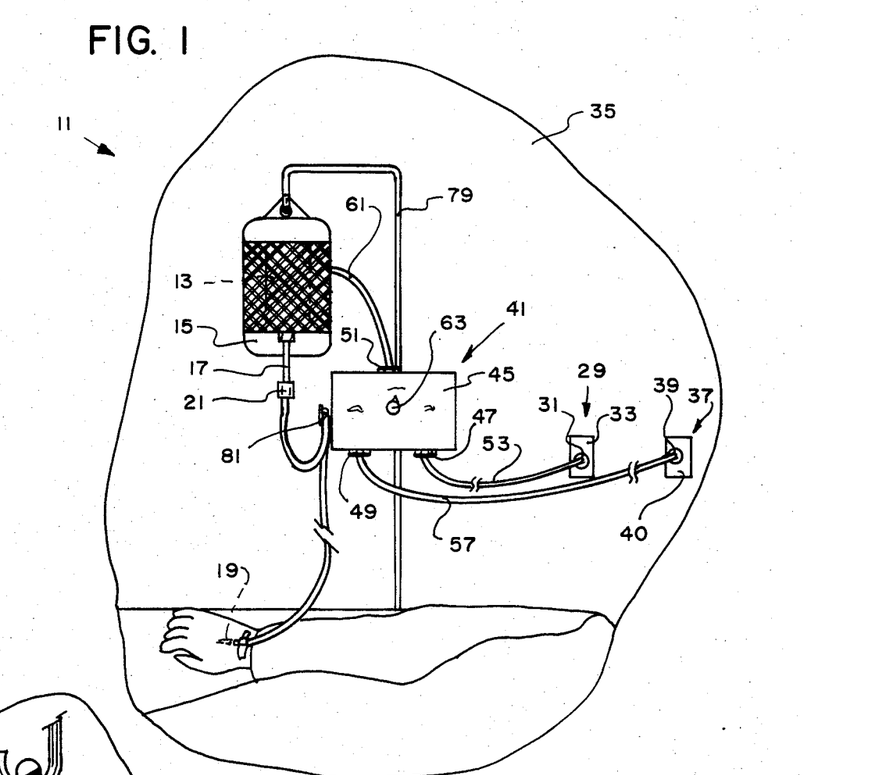
FIG. 1 is a somewhat diagrammatic view of a first embodiment of the pressure infusion system of the present invention shown in operation.
Figure 2:
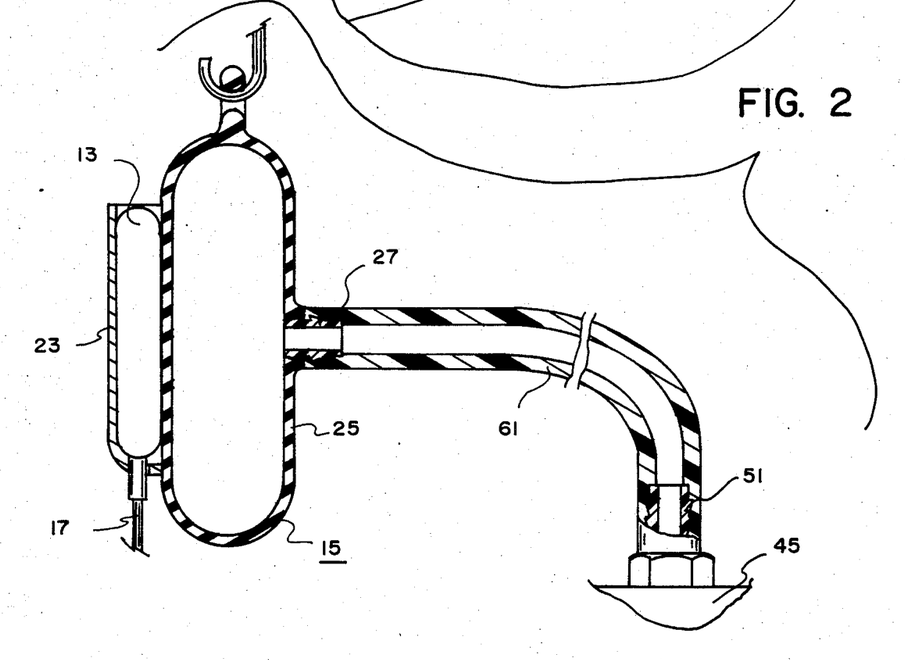
FIG. 2 is an enlarged sectional view of a portion of FIG. 1.
Figure 3:
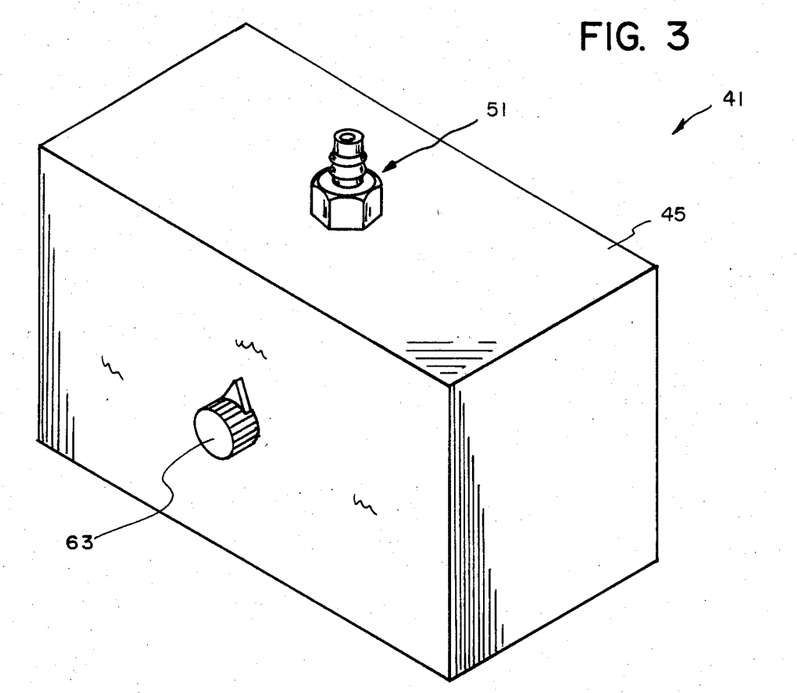
FIG. 3 is a perspective view of the control means of the system of FIG. 1.
Figure 4:
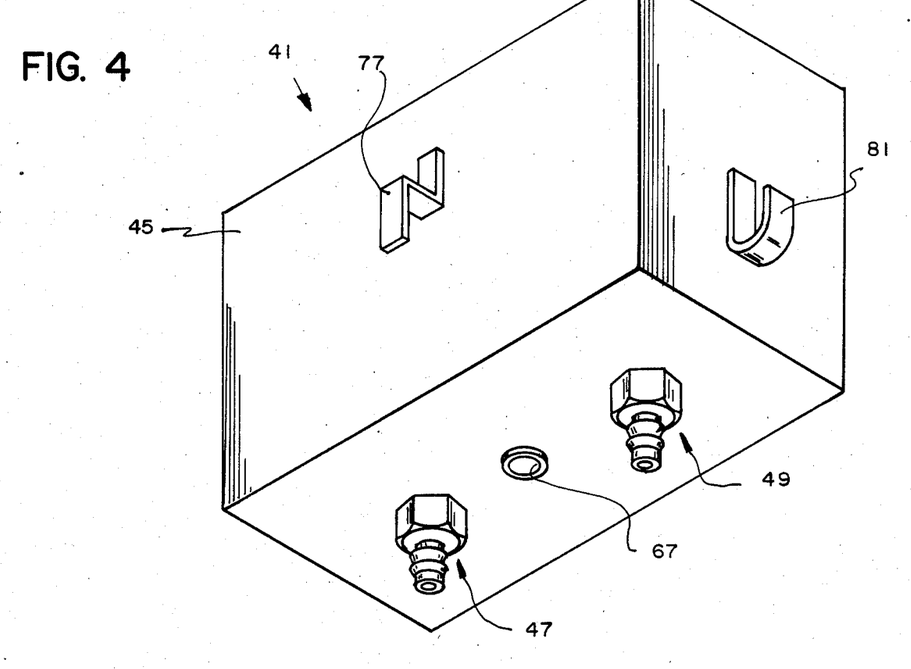
FIG. 4 is a perspective view of the control means of the system of FIG. 1 taken from a different angle than FIG. 3.

A support hook member 77 is preferably attached to the exterior of the housing member 45 for allowing the housing member 45 to be hung on a generally upright support member 79 substantially adjacent the flexible bag 13 which may also be hung on the support member 79 (see, in general, FIGS. 1 and 4). Thus, the support member 79 may consist of any typical and well-known "IV" support or pole well known to those skilled in the art. Another hook member 81 may be provided on the side of the housing member 45 for suporting the infusion line (i.e., the tube 17) and the like providing such line from touching the floor (see FIGS. 1 and 4).

As thus constructed and used, the system 11 is adapted to deliver a constant 300 millimeters of mercury positive pressure and approximately 500 millimeters of mercury (9.7 pounds per square inch gauge) negative pressure, depending on the pressure of the pressure source or means 29 and the vacuum source or means 37. The positive pressure is obtained from some positive pressure source such as the in-house oxygen or air supply which is available in all surgery suites and the like. The negative pressure is obtained from some vacuum source such as the in-house vacuum simply which is also available in all surgery suites and the like. The positive pessure source is reduced to a constant 300 millimeters of mercury by the use of the regulator means 65. As a safety feature, the high pressure relief valve means 67 is incorporated into the pressure supply lines which will open to the atmosphere should the pressure exceed ten percent of regulated value. The regulated positive pressure is supplied to one of two input ports of a three-position, three-way valve with the negative pressure supplied directly to the other input port of the valve. It should be noted that two or more valves may be ganged together to obtain a multiple output device. The system 11 allows positive pressure to be quickly applied to a typical pressure cuff to inflate the bladder thereof and to allow a vacuum to be applied thereto to quickly and actively deflate the bladder of the pressure cuff to allow quick replacement of the fluid containing bag.

A second embodiment of the present invention is shown in FIGS. 6-10. The pressure infusion system 2.11 of the second embodiment of the present invention is also of the type that includes a flexible bag 2.13 for containing a quantity of liquid to be infused, a pressure means 2.15 for selectively applying pressure to the bag 2.13 to force the liquid from the bag 2.13 and a tube 2.17 extending from the bag 2.13 to a needle 2.19 for being inserted into a patient's body (see FIG. 6). The pressure means 2.15 may consist of any typical, well-known pressure infusion cup as disclosed above relative to the first embodiment of the present invention and typically includes an inflatable bladder 2.25 for being mounted with respect to the bag 2.13 so that fluid will be forced from the bag 2.13 when the bladder 2.25 is inflated. The bladder 2.25 is provided with a port 2.27 for allowing air to be forced into the bladder 2.25 to inflate the bladder 2.25 and for allowing air to exit the bladder 2.25 to allow the bladder 2.25 to deflate. For a more specific understanding of the bag 2.13, pressure means 2.15 and associated structure, please refer to the above disclosure of the similar components of the first embodiment of the present invention.

Figures 6, 7, 8:
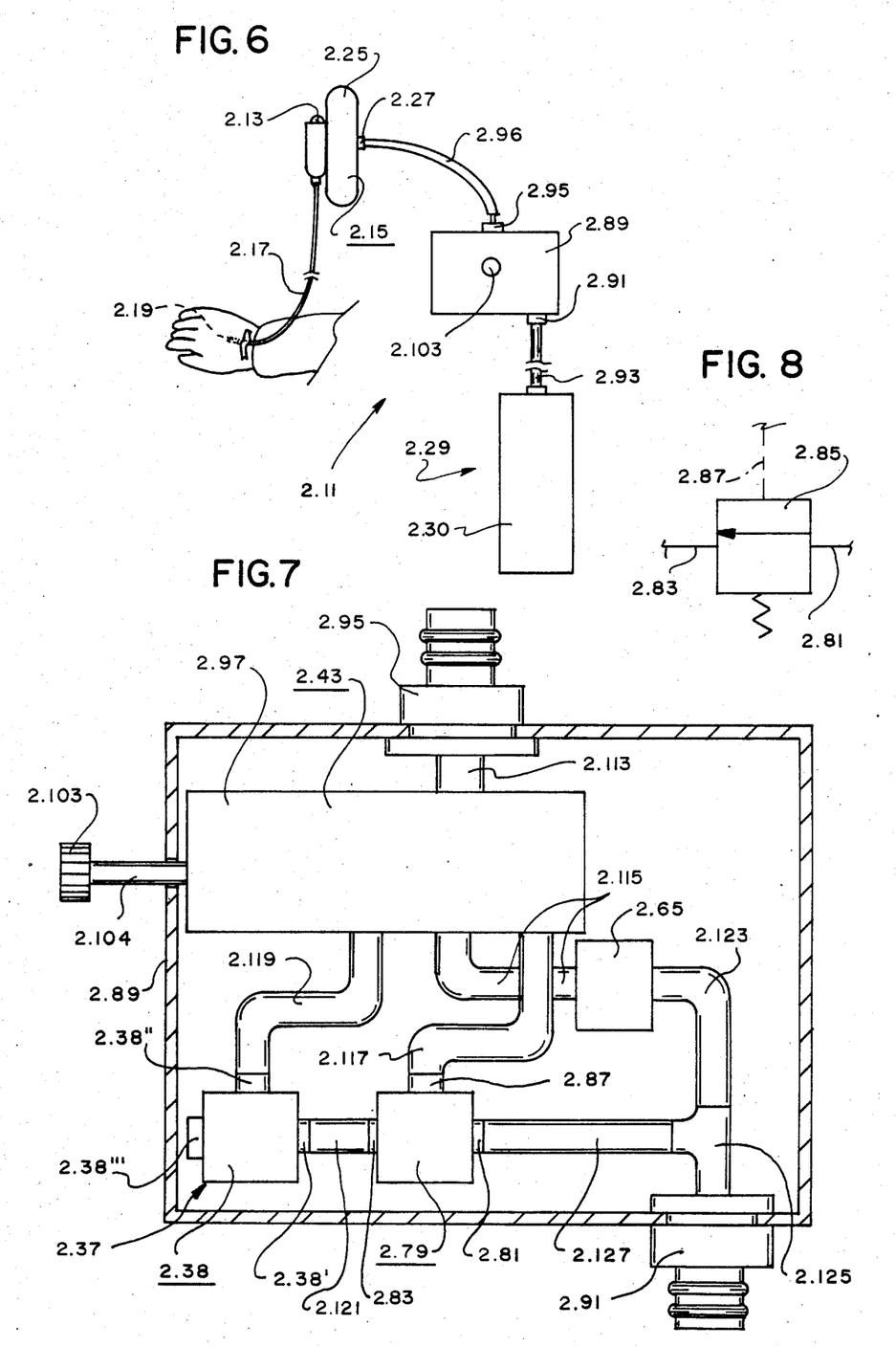
FIG. 6 is a somewhat diagrammatic view of a second embodiment of the pressure infusion system of the present invention shown in operation.
FIG. 7 is a sectional view of a portion of the control means and associated structure of the system of FIG. 6.
FIG. 8 is a graphic symbol of the normally closed valve member and associated structure of the pilot valve means of the system of FIG. 6.

The pressure infusion system 2.11 includes a pressurized fluid means 2.29 coupled to the bladder 2.25 for quickly inflating the bladder 2.25 (see FIG. 6). The term "pressurized fluid" as used herein includes pressurized air, pressurized gas, and the like. The pressurized fluid means 2.29 may consist of the typical pressurized gas source for supplying oxygen and the like to a patient, such as a typical pressurized gas outlet port mounted on the wall of a hospital room or the like as hereabove discussed relative to the first embodiment of the present invention. On the other hand, the pressurized fluid means 2.29 may consist of a portable tank 2.40 of pressurized fluid, such as a typical oxygen tank (see FIG. 6) well known to those skilled in the art for supplying oxygen to a patient whereby the pressure infusion system 2.11 may be portable.

The system 2.11 also includes a vacuum means 2.37 (see FIG. 7) coupled to the bladder 2.25 for quickly deflating the bladder 2.25 (e.g., for quickly removing the pressurized fluid from the bladder 2.25 after the pressurized fluid has inflated the bladder 2.25 to force the liquid from the bag 2.13) to allow the bag 2.13 to be quickly replaced with a full bag. The vacuum means 2.37 preferably consists of a typical vacuum pump 2.38 having a first inlet port 2.38' for being coupled to a source of pressurized fluid such as the pressurized fluid means 2.29, a second inlet port 2.38" for pumping fluid from a desired location, such as the bladder 2.25 when pressurized fluid is applied to the first inlet port 2.38' and an exhaust port 2.38'" for allowing fluid from the first and second inlet ports 2.38', 2.38" to exit the vacuum pump 2.38 (see FIG. 7). Such vacuum pumps are well known to those skilled in the art. Thus, the vacuum pump 2.38 may consist of the vacuum pump model M32, article number 31.01.043 of PIAB USA, INC., 65 Sharp St., Hingham, Mass. 02043.

Figure 9:
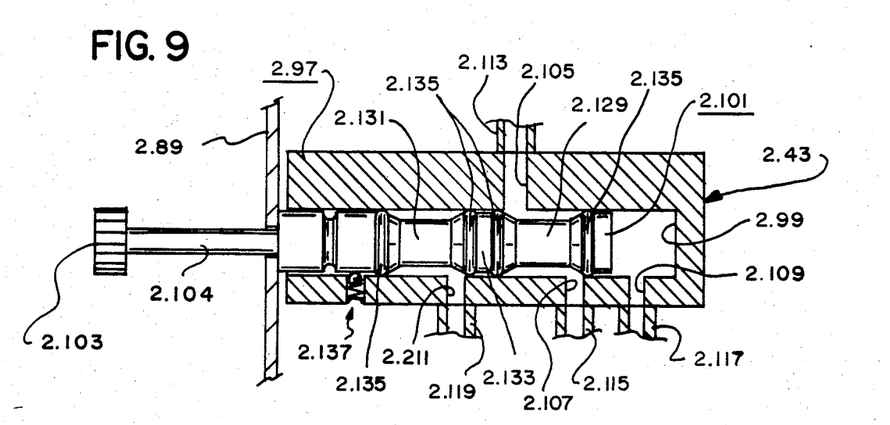
FIGS. 9, 10 and 11 are somewhat diagrammatic views of the valve means of the system of FIG. 6 showing the various positions of the valve means.
Figure 10:
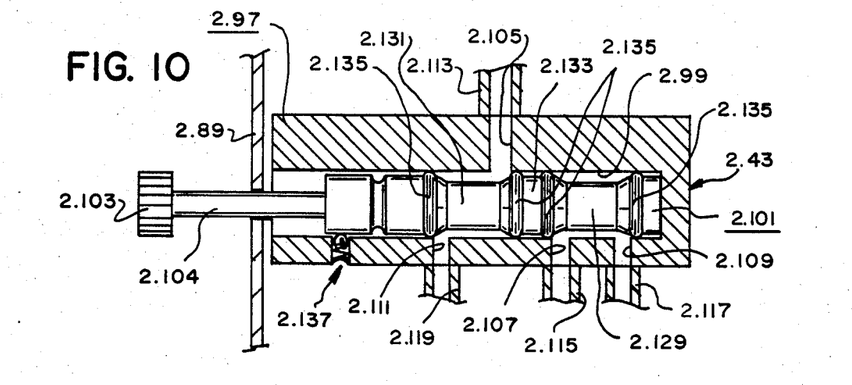

The system 2.11 includes a valve means 2.43 (see FIGS. 7 and 9-11) interposed between the pressurized fluid means 2.29 and the bladder 2.25 and between the vacuum means 2.37 and the bladder 2.25 for movement between a first position in which the pressurized fluid means 2.29 is allowed to inflate the bladder 2.25 (see FIG. 9) and a second position in which the vacuum means 2.37 is allowed to deflate the bladder 2.25 (see FIG. 10).

The system 2.11 preferably includes a regulator means 2.65 (see FIG. 7) for regulating the pressure of the pressurized fluid. The regulator 2.65 preferably consists of any typical, well-known high pressure relief valve means or the like for regulating the input fluid pressure and to provide a predetermined output fluid pressure despite any fluctuations in the input fluid pressure from the pressurized fluid means 2.29 and the preventing the pressure of the pressurized fluid from exceeding a predetermined amount as it is supplied to the pressure means 2.15. The regulator means 2.65 preferably maintains the positive pressure of the system 2.11 at a constant 300 mm of mercury (5.8 pounds per square inch gage). The regulator means 2.65 is preferably positioned between the pressurized fluid means 2.29 and the valve means 2.43.

The system 11 preferably includes a pilot valve means 2.79 (see FIGS. 7 and 8) for movement to an opened position when the valve means 2.43 is moved to the second position. The pilot valve means 2.79 is positioned between the pressurized fluid means 2.29 and the vacuum pump 2.38 to allow the flow of pressurized fluid from the pressurized fluid means 2.29 to the vacuum pump 2.38 when the valve means 2.43 is in the second position. The pilot valve means 2.79 may be of any typical construction and operation well known to those skilled in the art. Preferably, the pilot valve means 2.79 includes an inlet port 2.81, an outlet port 2.83, a normally closed valve member 2.85 for normally closing the passage between the inlet and outlet ports 2.81, 2.83, and a pilot or control port 2.87 for being coupled to a source of pressurized fluid and for causing the valve member 2.85 to move to an opened position when pressurized fluid passes through the control port 2.87 to thereby allow free passage between the inlet and outlet ports 2.81, 2.83 (see FIGS. 7 and 8).

The vacuum pump 2.38, valve means 2.43, regulator means 2.65 and pilot valve means 2.79 are preferably mounted within a box-like housing member 2.89 which may be constructed of cast aluminum or the like. The housing member 2.89 is preferably provided with a pressurized fluid port 2.91 (see FIGS. 6 and 7) substantially identical to the pressurized gas port 47 of the first embodiment of the present invention. The system 2.11 preferably includes a pressurized fluid inlet conduit 2.93 (see FIG. 6) for coupling the pressurized fluid 2.91 to the pressurized fluid means 2.29. The housing member 2.89 is also provided with an outlet port 2.95 (see FIGS. 6 and 7) substantially identical to the outlet port 51 of the first embodiment of the present invention. A conduit 2.96 (see FIG. 6) is provided for extending between the outlet port 2.95 and the port 2.27 of the bladder 2.25.

Figure 11:
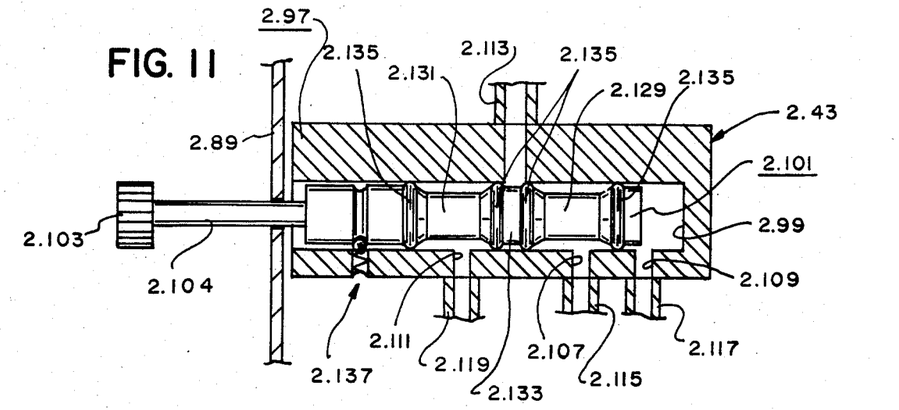

The valve means 2.43 preferably has a body 2.97 having an internal cavity 2.99 therein and having a plunger 2.101 slidably mounted within the cavity 2.99 (see FIGS. 9-11). The plunger 2.101 is attached to a handle 2.103 located on the exterior of the housing member 2.89 by way of a shaft 2.104 or the like for allowing the plunger 2.101 to be moved back and forth within the cavity 2.99, thus allowing the valve means 2.43 to be moved between the first and second positions. The body 2.97 has a first port 2.105, a second port 2.107, a third port 2.109 and a fourth port 2.111 communicating with the internal cavity 2.99 thereof. The first port 2.105 is coupled to the outlet port 2.95 of the housing member 2.89 by way of a conduit 2.113 or the like (see FIGS. 7 and 9-11). The second port 2.107 is coupled to the outlet port of the regulator means 2.65 by a conduit 2.115 or the like (see FIGS. 7 and 9-11). The third port 2.109 is coupled to the control port 2.87 of the pilot valve means 2.79 by a conduit 2.117 or the like (see FIGS. 7 and 9-11). The fourth port 2.111 is coupled to the second inlet port 2.38" of the vacuum pump 2.38 by a conduit 2.119 (see FIGS. 7 and 9-11). The outlet port 2.83 of the pilot valve means 2.79 is coupled to the first inlet port 2.38' of the vacuum pump 2.38 by a conduit 2.121 or the like (see FIG. 7). The inlet port of the regulator means 2.65 is coupled to the pressurized fluid port 2.91 of the housing member 2.89 by a conduit 2.123 or the like through a first branch of a tee-fitting 2.125 or the like (see FIG. 7). The inlet port 2.81 of the pilot valve means 2.79 is coupled to the pressurized fluid port 2.91 of the housing member 2.89 by a conduit 2.127 through a second branch of the tee-fitting 2.125 or the like (see FIG. 7). The various conduits are coupled to the various ports and the like in any manner well known to those skilled in the art such as by way of press-on type fittings (not shown) to create a substantially fluid-tight connection.

The plunger 2.101 has a first groove 2.129 thereabout, a second groove 2.131 thereabout, and a midportion 2.133 between the first and second grooves 2.129, 2.131 (see FIGS. 9-11). A plurality of seal members 2.135 such as typical O-rings per the like are provided on the plunger 2.101 for forming fluid-tight seals between the plunger 2.101 and the internal cavity 2.99 of the body 2.97 and for separating the first and second grooves 2.129, 2.131 and the midportion 2.133 in a manner which will be apparent from FIGS. 9-11. When the valve means 2.43 is in the first position with the plunger 2.101 fully pulled out as shown in FIG. 9, pressurized fluid will be allowed to pass from the second port 2.107 around the first groove 1.129 and out the first port 2.105 to inflate the bladder 2.25. When the valve means 2.43 is in the second position with the plunger fully pushed in as shown in FIG. 10, pressurized fluid will be allowed to pass through the second port 2.107, about the first groove 2.129 and out the third port 2.109 to cause the valve member 2.85 to open allowing pressurized fluid at full strength to pass through the pilot valve means 2.79 and through the vacuum pump 2.38 thereby drawing fluid from the bladder 2.25 through the first port 2.105, around the second groove 2.131, through the fourth port 2.111 through the second inlet port 2.38" and out the exhaust port 2.38''' to thereby quickly and positively deflate the bladder 2.25. The valve means 2.43 preferably has a third position with the plunger 2.101 substantially midway between the fully pulled out and the fully pushed in positions as shown in FIG. 11 whereby the first, second, third and fourth ports 2.105, 2.107, 2.109, 2.111 are closed (i.e., sealed from one another). A ball and detent means 2.137 or the like, of any typical construction well known to those skilled in the art is preferably provided to urgably hold the plunger 2.101 in the third position (see FIG. 11).

As thus constructed and used, the system 2.11 is adapted o deliver a constant 300 millimeters of mercury positive pressure and approximately 700 millimeters of mercury (13.6 pounds per square inch gauge) negative pressure, depending on the pressure of the pressure source or means 2.29 and the vacuum source or means 2.37. The positive pressure is obtained from some positive pressure source such as the in-house oxygen or air supply which is available in all surgery suites and the like, a portable oxygen tank, or the like. The negative pressure is obtained from some vacuum source such as the vacuum pump 2.38 which converts a positive pressure of approximately 55 pounds per square inch gauge into approximately 700 millimeters of mercury by venturi action well known to those skilled in the art. The positive pressure source is reduced to a constant 300 millimeters of mercury by the use of the regulator means 2.65. The regulated positive pressure is supplied to one port of the three-position valve means 2.43. The negative pressure is applied to another port of the three-position valve means 2.43 only when the valve 2.43 is in the vacuum position (FIG. 10) to allow communication between the vacuum means 2.37 and the outlet port 2.95. When the valve means 2.43 is in the vacuum position as shown in FIG. 10, the regulated positive pressure is in communication with the pilot valve means 2.67. When the regulated positive pressure is applied to the pilot valve means 2.79, the normally closed valve member 2.85 is opened to allow communication between the positive unregulated pressure of approximately 55 pounds per square inch gauge and the vacuum means 2.37. It should be noted that two or more valves may be ganged together to obtain a multiple output device. The system 2.11 allows positive pressure to be quickly applied to a typical pressure cuff to inflate the bladder thereof and to allow a vacuum to be applied thereto to quickly and positively deflate the bladder of the pressure cuff to allow quick replacement of the fluid containing bag.

Although the present invention has been described and illustrated with respect to preferred embodiments thereof and preferred uses therefor, it is not to be so limited since changes and modifications can be made therein which are within the full intended scope of the invention.

We claim:

1. An improved pressure infusion system of the type including a flexible bag for containing a quantity of liquid to be infused into a patient, a pressure means for selectively applying pressure to said bag to force said liquid from said bag, wherein the improvement comprises:
   (a) pressurized fluid means for supplying pressurized fluid to said pressure means to cause said pressure means to apply pressure to said bag to force said liquid from said bag;
   (b) vacuum means for quickly and actively evacuating said pressurized fluid from said pressure means to allow said bag to be quickly removed from said pressure means and replaced with another bag; said vacuum means including a vacuum pump for creating a negative pressure to draw said pressurized fluid from said pressure means; said vacuum pump creating said negative pressure when pressurized fluid is supplied thereto; and
   (c) control means for controlling said pressurized fluid means and said vacuum means, said control means including a valve means for movement between a first position in which said pressurized fluid means is allowed to supply pressurized fluid to said pressure means, and a second position in which said vacuum means is allowed to remove said pressurized fluid from said pressure means; said control means including a regulator means for regulating the pressure of said pressurized fluid before it is supplied to said pressure means; said pressurized fluid means being allowed to supply pressurized fluid to said vacuum pump when said valve means is in said second position.

2. An improved pressure infusion system of the type including a flexible bag for containing a quantity of liquid to be infused, a pressure means for selectively applying pressure to said bag to force said liquid from said bag, wherein the improvement comprises:
   (a) pressurized fluid means for supplying pressurized fluid to said pressure means to cause said pressure means to apply pressure to said bag to force said liquid from said bag;
   (b) vacuum means activated by pressurized fluid from said pressurized fluid means for quickly removing said pressurized fluid from said pressure means; and
   (c) control means for controlling said pressurized fluid means and said vacuum means, said control means including a valve means for movement between a first position in which said pressurized fluid means is allowed to supply pressurized fluid to said pressure means, and a second position in which said pressurized fluid means is allowed to supply pressurized fluid to said vacuum means to remove said pressurized fluid from said pressure means, said control means including a regulator means for regulating the pressure of said pressurized fluid before it is supplied to said pressure means and including means for allowing said pressurized fluid to by-pass said regulator means and pass directly to said vacuum means when said valve means is in said second position.

3. An improved pressure infusion system of the type including a flexible bag for containing a quantity of liquid to be infused, a pressure means for selectively applying pressure to said bag to force said liquid from said bag, wherein the improvement comprises:
   (a) pressurized fluid means for supplying pressurized fluid to said pressure means to cause said pressure means to apply pressure to said bag to force said liquid from said bag;
   (b) vacuum means for quickly removing said pressurized fluid from said pressure means; and
   (c) control means for controlling said pressurized fluid means and said vacuum means, said control means including a valve means for movement between a first position in which said pressurized fluid means is allowed to supply pressurized fluid to said pressure means, and a second position in which said vacuum means is allowed to remove said pressurized fluid from said pressure means; said control means including a regulator means for regulating the pressure of said pressurized fluid before it is supplied to said pressure means; said vacuum means including a vacuum pump for creating a negative pressure to draw said pressurized fluid from said pressure means; said vacuum pump creating said negative pressure when pressurized fluid is supplied thereto; said pressurized fluid means being allowed to supply pressurized fluid to said vacuum pump when said valve means is in said second position; said control means including a pilot valve means for allowing said pressurized fluid from said pressurized fluid means to by-pass said regulator means and pass directly to said vacuum pump when said valve means is in said second position.

4. The improvement of claim 3 in which said pressurized fluid means includes a portable oxygen tank.

* * * * *